(12) United States Patent  
MacDougall et al.

(10) Patent No.: US 11,786,749 B2  
(45) Date of Patent: Oct. 17, 2023

(54) TIME MULITPLEXED DOSIMETRY SYSTEM AND METHOD

(71) Applicant: Lumeda Inc., Rocky Hill, CT (US)

(72) Inventors: Trevor MacDougall, Dartmouth, MA (US); Yi Yang, Storrs, CT (US)

(73) Assignee: Lumeda Inc., Rocky Hill, CT (US)

( * ) Notice: Subject to any disclaimer, the term of this patent is extended or adjusted under 35 U.S.C. 154(b) by 52 days.

(21) Appl. No.: 17/997,942

(22) PCT Filed: May 4, 2021

(86) PCT No.: PCT/US2021/030539  
§ 371 (c)(1),  
(2) Date: Nov. 4, 2022

(87) PCT Pub. No.: WO2021/226001  
PCT Pub. Date: Nov. 11, 2021

(65) Prior Publication Data  
US 2023/0173299 A1    Jun. 8, 2023

Related U.S. Application Data

(60) Provisional application No. 63/020,142, filed on May 5, 2020.

(51) Int. Cl.  
*A61N 5/06* (2006.01)  
*A61N 5/067* (2006.01)

(52) U.S. Cl.  
CPC ............. *A61N 5/062* (2013.01); *A61N 5/067* (2021.08); *A61N 2005/0628* (2013.01); *A61N 2005/063* (2013.01)

(58) Field of Classification Search  
None  
See application file for complete search history.

(56) References Cited

U.S. PATENT DOCUMENTS

| | | | | |
|---|---|---|---|---|
| 4,761,047 A | * | 8/1988 | Mori | A61N 5/0616 385/115 |
| 4,907,132 A | * | 3/1990 | Parker | D03D 15/37 385/100 |
| 5,445,608 A | * | 8/1995 | Chen et al. | A61N 5/0601 604/20 |
| 5,474,528 A | * | 12/1995 | Meserol | A61N 5/062 604/20 |

(Continued)

OTHER PUBLICATIONS

Dickey et al. "Fractionated PDT light delivery system based upon fibre optic switching technology." European Conference on Biomedical Optics 2003 (Date of Publicaition: Jun. 22, 2003).

*Primary Examiner* — Carl H Layno  
*Assistant Examiner* — Manolis Pahakis  
(74) *Attorney, Agent, or Firm* — Matthew J Patterson

(57) ABSTRACT

A therapeutic light delivery apparatus and method are disclosed. The apparatus includes a light source, a plurality of light emitting devices paired with a plurality of light detecting devices, wherein each of the light emitting devices is in optical communication with a channel of a delivery optical switch and each of the plurality of light detection devices is in optical communication with a channel of a detection optical switch. The plurality of light emitting devices are fixedly positioned within an applicator light flap. The system further includes an optical detector in optical communication with the detector optical switch. The system further includes an opto-electronic controller that controls delivery optical switch, the detector optical switch and the light source.

6 Claims, 3 Drawing Sheets

(56) References Cited

U.S. PATENT DOCUMENTS

| | | | |
|---|---|---|---|
| 5,489,279 A * | 2/1996 | Meserol | A61F 13/02 604/20 |
| 5,505,726 A * | 4/1996 | Meserol | A61F 13/0213 606/17 |
| 5,944,748 A * | 8/1999 | Mager et al. | A61N 5/0601 606/9 |
| 6,385,221 B1* | 5/2002 | Neuberger | H01S 5/4031 372/38.02 |
| 6,645,230 B2* | 11/2003 | Whitehurst | A61N 5/0613 607/88 |
| 6,743,249 B1* | 6/2004 | Alden | A61N 5/0601 606/1 |
| 6,989,023 B2* | 1/2006 | Black | A61H 23/0245 607/90 |
| 6,991,644 B2* | 1/2006 | Spooner et al. | A61N 5/0614 606/9 |
| 7,448,775 B2* | 11/2008 | Parker et al. | G02B 6/0036 362/330 |
| 7,686,839 B2* | 3/2010 | Parker | A61N 5/0616 607/93 |
| 8,372,063 B2* | 2/2013 | Williams | A61N 5/06 385/45 |
| 8,462,292 B2* | 6/2013 | Parker et al. | G02B 6/0046 362/616 |
| 8,702,640 B2* | 4/2014 | Dacey, Jr. et al. | A61F 2/30 604/9 |
| 8,926,959 B2* | 1/2015 | Deisseroth et al. | A61K 48/0083 530/825 |
| 9,149,651 B2* | 10/2015 | Keltner et al. | A61N 5/062 |
| 10,064,940 B2* | 9/2018 | Nager | A61K 41/0052 |
| 10,166,402 B2* | 1/2019 | Brennan et al. | A61F 13/00068 |
| 10,500,413 B2* | 12/2019 | Altshuler et al. | A61N 5/0616 |
| 10,765,767 B2* | 9/2020 | Zaborsky | A61M 16/0816 |
| 11,344,742 B2* | 5/2022 | Shafirstein et al. | A61N 5/0601 |
| 2003/0009205 A1* | 1/2003 | Biel | A61N 5/0601 607/88 |
| 2003/0202338 A1* | 10/2003 | Parker | F21V 5/10 362/602 |
| 2004/0267335 A1* | 12/2004 | Tulip et al. | A61N 5/062 607/89 |
| 2005/0063194 A1* | 3/2005 | Lys et al. | B60Q 3/85 362/489 |
| 2005/0152416 A1* | 7/2005 | Chang | H01S 5/06804 372/38.02 |
| 2006/0020309 A1* | 1/2006 | Altshuler et al. | A61H 39/002 607/88 |
| 2010/0016783 A1* | 1/2010 | Bourke, Jr. et al. | A61P 35/00 378/65 |
| 2010/0331927 A1* | 12/2010 | Cottrell et al. | A61N 5/062 607/88 |
| 2011/0295343 A1* | 12/2011 | Bornstein et al. | A61N 5/0624 607/88 |
| 2013/0030264 A1* | 1/2013 | Gopalakrishnan et al. | H05B 45/12 250/201.1 |
| 2015/0244492 A1* | 8/2015 | Lee | H04Q 11/0005 398/48 |
| 2016/0030765 A1* | 2/2016 | Towne et al. | A61B 18/18 607/88 |
| 2019/0246463 A1* | 8/2019 | Williams et al. | A61N 5/06 |
| 2022/0001193 A1* | 1/2022 | Zhu et al. | A61N 5/062 |

* cited by examiner

TIME MULITPLEXED DOSIMETRY SYSTEM AND METHOD

CROSS REFERENCE TO RELATED APPLICATIONS

This application claims the benefit of U.S. Provisional Pat. Application Serial No. 63/020142 having a filing date of 5 May 2020 as well as Patent Cooperation Treaty Pat. Application Serial No. PCT/US21/30539 filed 04 May 2021. The disclosure of the application above is incorporated herein by reference in its entirety.

FIELD OF THE DISCLOSURE

The present disclosure relates to photodynamic therapy.

DESCRIPTION OF THE RELATED ART

Light therapy can be used for the treatment of conditions in multiple ways. For example, light therapies involve the delivery of a therapeutic light through a fiber optic device placed proximal to or within a target tumor.

Light therapies can be combined with prior administration of light sensitizing medication (i.e., photosensitizer) that absorbs the therapeutic light and interacts with surrounding tissue constituents (e.g., oxygen) to generate reactive species that can destroy the target tissue. This form of therapy is known as photodynamic therapy ("PDT"). PDT uses light (such as light provided by a laser) to activate a non-toxic photosensitizer.

In addition, or alternatively, the energy of the light can be absorbed by blood or external additives (such as metal particles) that convert the light energy into heat, to induce destruction of the target tumor tissue.

In typical prior art light therapies, it can be important that the entire tumor be illuminated with sufficient dose light in order to administer a successful treatment. It is a deficiency in the prior art that it is difficult to know where and how much light is delivered to the tumor or tissue.

An example of a photodynamic light therapy (PDT) delivery system and method is disclosed in U.S. Pat. Application No. 20180207442 wherein the PDT is used for the treatment of a tissue. A plurality of light-transmitting catheters (LTCs) having diffusers mounted at a distal end are provided and placed in the tissue according to a pre-determined treatment plan, wherein an LTC includes a first treatment fiber disposed therethrough, and an LTC includes a dosimetry fiber disposed therethrough. A dose light is provided to the tissue via the light diffusers by way of the first treatment fiber according to the pre-determined treatment plan. The diffusers are manually positioned in the target tissue and the light is monitored using the dosimetry fiber.

Another example of PDT can be found in U.S. Pat. Application No. 20180207441 wherein a system and method are disclosed that use a flexible guide (flap) having optical fibers that emit light from a distal end to control the delivery of light dose to a treatment area. This approach overcomes the non-reliable delivery of light dose with a flap that conforms to the target area. Dosimetry control can be improved through the use of a computer controlled motor to move the laser fibers linearly within spheres at a known speed over the target tissue.

Referring to FIG. 1, there is shown cylindrical light diffuser 1 disposed within catheter 2 and optically connected to optical fiber 5 and cylindrical light diffuser 3 disposed within catheter 4 and optically connected to optical fiber 6. It can be seen that cylindrical light diffuser 1 is disposed at a first position along the linear length of catheter 2 and cylindrical light diffuser 3 is positioned a second position (relative to the first position) along the linear length of catheter 4. It is known in the prior art to physically move the cylindrical light diffusers within the catheter by manual means and automated means to position light emitted from the cylindrical light diffusers over a predetermined target area. Now referring to FIG. 2, a prior art PDT system 10 is shown that includes an optoelectronic instrument 11 and a light flap 7. Light flap 7, can comprise a Freiburg flap, and includes cylindrical light diffusers 1, 3, 15, 17 which may or may not be positioned within catheters. Light flap 7 further includes detector fibers 19, 20, 21, 22 to detect therapy light emitted from cylindrical light diffusers 1, 3, 15, 17 respectively. It is typical in such a prior art embodiment that optoelectronic instrument 11 includes a plurality of lasers, and a plurality of detectors. In this particular example, individual lasers 23, 24, 25, 26 are optically coupled to cylindrical light diffusers 1, 3, 15, 17 respectively by optical fibers. Further, detector fibers 19, 20, 21, 22 are optically coupled to individual detectors 27, 28, 29, 30 respectfully. Optoelectronic instrument 11 further includes the control hardware and software for the lasers and detectors, among other components. It is a known problem with such a PDT system 10 that by using a separate laser and detector for each diffuser and detector, the PDT system is expensive, cumbersome, difficult to scale and, due to the fact there are so many components, reliability and accuracy are problematic.

What is needed is a PDT system that has improved accuracy and performance is simpler, less expensive, more reliable and easier to scale than that which is found in the prior art.

SUMMARY OF THE DISCLOSURE

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes an optical light delivery system. The optical light delivery system also includes a light source, an opto-electronic controller having a computer processor and a light device controller, a delivery optical switch having a plurality of optical output channels, the delivery optical switch being optically coupled to the light source and electrically coupled to the opto-electronic controller, a plurality of light emitting devices, each light emitting device of the plurality of light emitting devices being optically coupled to a respective optical output channel of the plurality of optical output channels, and the opto-electronic controller configured to control the delivery optical switch to selectively optically couple the light source with each of the plurality of optical output channels to produce an irradiance level for each of the plurality of the light emitting devices.

Implementations may include one or more of the following features. The optical light delivery system where the opto-electronic controller is further configured to produce the irradiance level for each of the plurality of the light emitting devices for a dwell time to produce a desired complete target. Each of the plurality of light emitting devices are statically positioned at a predetermined location in a respective longitudinal channel of the plurality of longitudinal channels. The optical light delivery system may include: an optical detector, a detector optical switch having a plurality of optical input channels, the detector optical switch electrically coupled to the opto-electronic controller, a plurality of detector fibers, each detector fiber of the plurality of detector fibers being positioned proximate a respective light emitting device of the plurality of light emitting devices and configured to detect at least one optical parameter from each of the respective light emitting devices, each detector fiber of the plurality of detector fibers being optically coupled to a respective optical input channel of the plurality of optical input channels, the opto-electronic controller configured to control the detector optical switch to selectively optically couple each of the plurality of optical input channels to the optical detector, and the optical detector adapted to produce an output signal based on the at least one optical parameter from the plurality of detector fibers. The opto-electronic controller is further configured to receive the output signal and adjust the at least one optical parameter and the dwell time for each respective light emitting device of the plurality of the light emitting devices in accordance with a predetermined treatment plan. The opto-electronic controller is configured to operate in a closed loop control. The predetermined treatment plan is a photodynamic therapy plan. The delivery optical switch and detector optical switch each may include a MEMS type optical switch. The light source may include at least one semiconductor laser. Each of the light emitting devices of the plurality of light emitting devices have a length and where the length can may include a plurality of different lengths. Together with the irradiance level and the dwell time, the plurality of different lengths are chosen to produce the desired complete target.

One general aspect includes a method for providing photodynamic therapy. The method also includes determining a photodynamic therapy plan for each of a plurality of light emitting devices to produce an irradiance pattern for a target tissue, developing an initial dwell time plan and an initial power level plan for each of the plurality of light emitting devices, positioning the plurality of light emitting devices at predetermined different positions proximate the target tissue, selecting sequentially each of the light emitting devices, delivering therapy light to the light emitting devices at an initial power level in accordance with the initial power level plan, detecting an optical parameter of an actual therapy light, comparing the optical parameter to the photodynamic therapy plan, adjusting the initial power level to an updated power level, calculating a new dwell time plan, summing a total dwell time and a total power level for each of the plurality of light emitting devices, and completing the irradiance pattern in accordance with the photodynamic therapy plan. Other embodiments of this aspect include corresponding computer systems, apparatus, and computer programs recorded on one or more computer storage devices, each configured to perform the actions of the methods.

Implementations may include one or more of the following features. The method for providing photodynamic therapy may include positioning the plurality of light emitting devices within a flexible applicator flap. The selecting step may include using an optical switch. The detecting step may include using a plurality of detector fibers where each of the plurality of detector fibers is paired with a respective light emitting device of the plurality of light emitting devices. The method for providing photodynamic therapy may include selecting sequentially the plurality of detector fibers in coordination with the paired respective light emitting device. The method for providing photodynamic therapy may include selecting a length for each of the plurality of light emitting devices One general aspect includes time multiplexed dosimetry system. The time multiplexed dosimetry system also includes a laser light source for producing a therapy light, a delivery system configured to deliver the therapy light to a target tissue, a detection system configured to monitor at least one parameter of the therapy light, and a control system configured to control the delivery system to produce an irradiance pattern over the target tissue. Other embodiments of this aspect include corresponding computer systems, apparatus, and computer programs recorded on one or more computer storage devices, each configured to perform the actions of the methods.

Implementations may include one or more of the following features. The time multiplexed dosimetry system where the delivery system may include a delivery optical switch for selectively coupling the therapy light to a plurality of cylindrical light diffusers and the control system is further configured to produce an irradiance level for each of the plurality of the light emitting devices. The delivery optical switch is controlled to produce the irradiance level for each of the plurality of the cylindrical light diffusers for a dwell time producing a desired complete target. The delivery further may include a flexible applicator flap having a plurality of longitudinal channels disposed therein and adapted to be positioned within a human body proximate the target tissue where each of the plurality of cylindrical light diffusers are statically positioned at a predetermined location in a respective longitudinal channel of the plurality of longitudinal channels. The detection system may include an optical detector, a plurality of detector fibers, each detector fiber of the plurality of detector fibers being positioned proximate a respective cylindrical light diffuser of the plurality of cylindrical light diffusers and configured to detect the at least one parameter of the therapy light from each of the respective cylindrical light diffusers, a detector optical switch for selectively coupling each detector fiber of the plurality of detector fibers, and where the control system controlling a position of the delivery optical switch and a position of the detector optical switch such that a pair of respective cylindrical light diffuser of the plurality of cylindrical light diffusers and a detector fiber of the plurality of detector fibers delivers the at least one parameter of the therapy light to the optical detector. The time multiplexed dosimetry system the control system is further configured to adjust the at least one parameter of the therapy light and the dwell time for each respective cylindrical light diffuser of the plurality of the cylindrical light diffusers in accordance with a predetermined treatment plan. The predetermined treatment plan is a photodynamic therapy plan. The delivery optical switch and detector optical switch each may include a MEMS type optical switch. Each of the cylindrical light diffusers of the plurality of cylindrical light diffusers have a length and where the length can may include a plurality of different lengths. Together with the irradiance level and the dwell time, the plurality of different lengths are chosen to produce the desired complete target. The laser light source may include at least one semiconductor laser. Implementations of the described techniques may include hardware, a method or process, or computer software on a computer-accessible medium.

BRIEF DESCRIPTION OF THE DRAWINGS

So that the manner in which the above-recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

DETAILED DESCRIPTION

In the following detailed description of the embodiments, reference is made to the accompanying drawings, which form a part hereof, and within which are shown by way of illustration specific embodiments by which the examples described herein may be practiced. It is to be understood that other embodiments may be utilized and structural changes may be made without departing from the scope of the disclosure.

The current disclosure is related to the control of a desired irradiance pattern and fluence of light directed to a target with the ability to alter the irradiance pattern to optimize the delivery of light to particular locations in an economical and efficient manner for PDT systems. This disclosure further relates to the ability to accurately measure the delivered irradiance and fluence.

Figure 1:
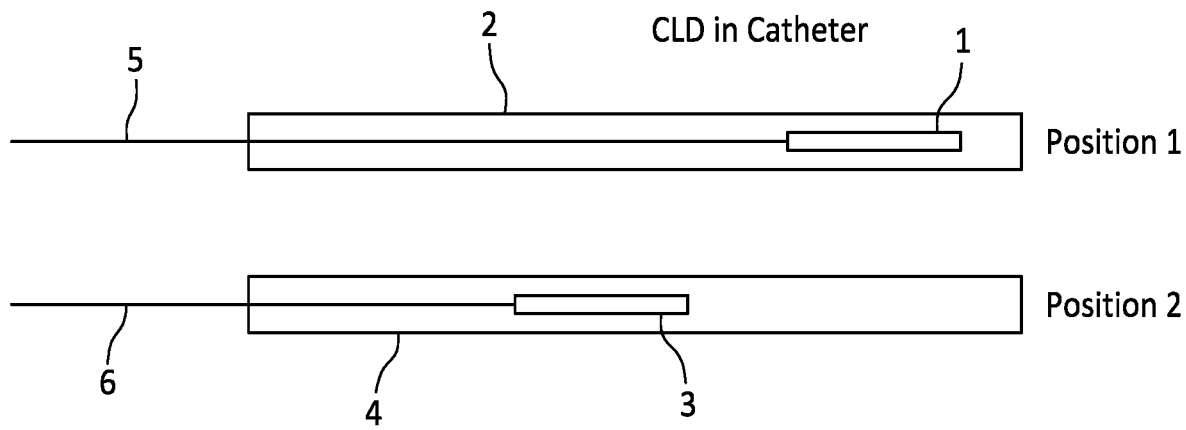
FIG. 1 is an illustration of a prior art cylindrical light diffuser and catheter arrangement.
Figure 2:
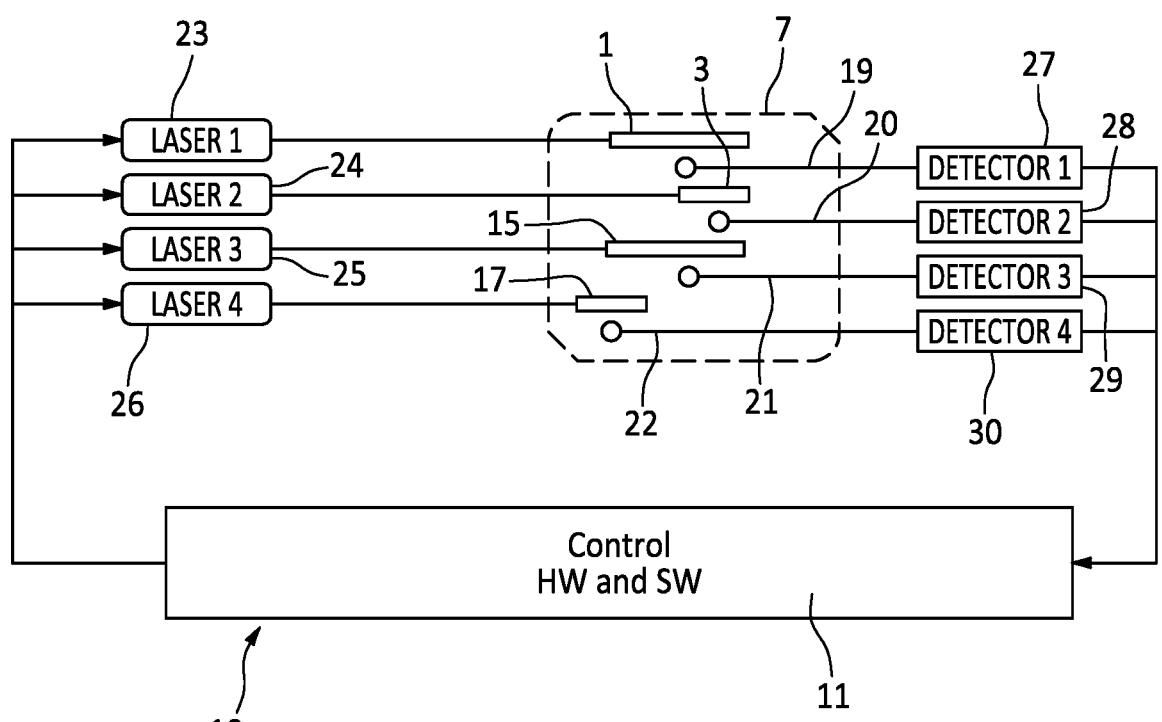
FIG. 2 is an illustration of a prior art PDT system.
Figure 3:
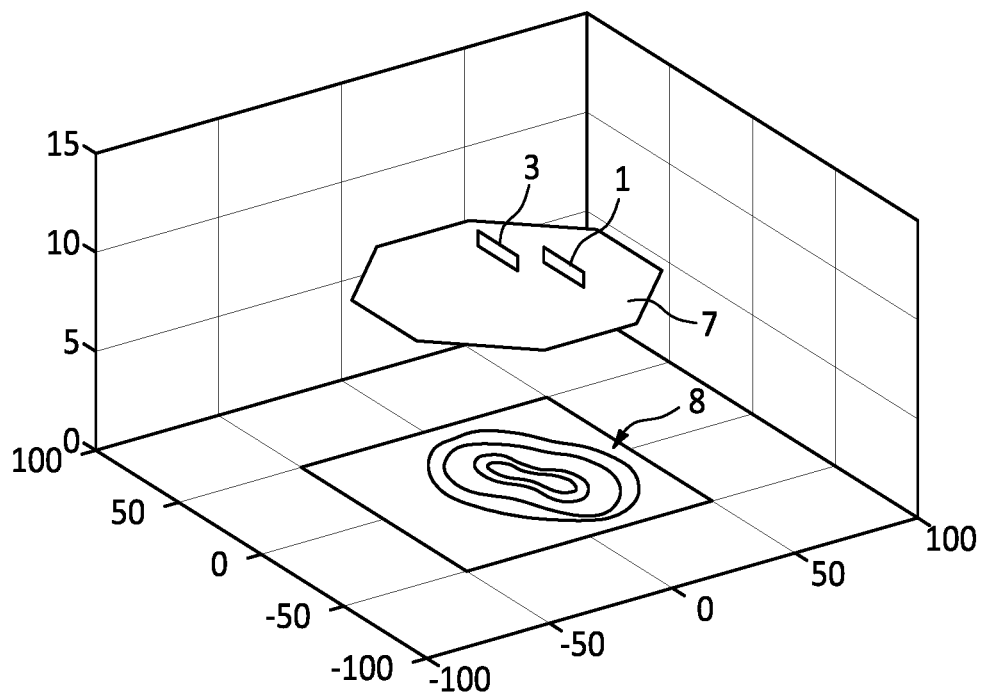
FIG. 3 is graphical representation of an irradiance profile of a PDT system in accordance with the present disclosure.

Referring now to FIG. 3, there is shown an apparatus and method of determining the irradiance pattern 8 of an embodiment of a PDT system wherein a plurality of cylindrical light diffusers, wherein cylindrical light diffusers 1, 3, are but two, which can be positioned inside catheters that are then placed inside the channels of an applicator light flap 7. The plurality of cylindrical light diffusers can include diffusers having different lengths and the diffusers are fixed within the channels of applicator flap 7 and can be individually addressed as will be disclosed in more detail herein after. Light flap 7 can comprise any known flexible applicator flap that facilitates the delivery of treatments of advanced cancers. Some known applicator flaps include a Freiburg flap manufactured by Elekta and a H.A.M. application available from Mick Radio-Nuclear Instruments. Light flap 7 can comprise a flexible pad of silicone rubber that is 8 mm thick and is light transmissive. An array of catheters can be embedded parallel to each other in longitudinal channels therein and in an embodiment are spaced 10 mm apart and produces a consistent light source-to-tissue distance of 5 mm. Light flap 7 conforms to the shape of surfaces to which it is applied. Light flap 7 can also include embodiments without catheters, alternate materials and custom shapes without departing from the scope of the present disclosure. Cylindrical light diffusers 1,3 are selectively optically coupled to a light source as will be disclosed in more detail herein after. The cylindrical light diffusers are configured to transmit light from the light source at a predetermined wavelength (nm), fluence (J/cm$^2$) and dwell time (s) to deliver a dosage of therapy light to a target area of a human body. One embodiment of a suitable cylindrical light diffuser is model RD-50 available from Rakuten Medical. The position of cylindrical light diffusers 1, 3 is fixed within flap 7 and the irradiance distribution is controlled to match the geometry of a target. Irradiance pattern 8 is determined based on a target geometry of target tissue to be treated using PDT. The target geometry can be determined using imaging data comprised of magnetic resonance images, x-rays, etc. and can be in a digital form and referenced to a location on a patient's body. Although disclosed herein above with respect to an embodiment of a PDT system having a light flap 7 having two cylindrical diffusers 1, 3 selected from therein, the plurality of other light diffusers are not shown for clarity sake. In some embodiments the cylindrical light diffusers have three states, namely on, off, and dwell time. The novelty of having a plurality of cylindrical light diffusers enables such a system to produce optimized treatment irradiance profiles with greater resolution in terms of spatial resolution, temporal resolution and dosimetry resolution. For example, in embodiments that include six light diffusers, which can be positioned adjacent to one another to form a 1x6 array or end-to-end to form a 2×3 array or other pattern within light flap 7, and each of the six light diffusers have three states, the plurality of choices from among the plurality of cylindrical light diffuser is $3^6$ or 64 cases each having a distinct irradiance profile array. Such embodiments provide greater spatial resolution to determine an optimized treatment irradiance profile that more closely matches the location, shape and size of a target tissue. It should be appreciated by those skilled in the art that light flap 7 having a plurality of channels can accommodate a relatively high number of cylindrical light diffusers (compared to the example of six) to provide for an even greater levels of resolution. For instance, embodiments having eight cylindrical light diffusers would provide $3^8$ or 6,561 distinct irradiance patterns, an embodiment having 16 cylindrical light diffusers would $3^{16}$ or 43,046,721 distinct irradiance patterns and so on. As will be disclosed herein after, the apparatus of the present disclosure enables the selective addressing of a subset of the plurality of cylindrical light diffusers to produce an irradiance pattern that substantially matches the target tissue.

Using this method and the system of the present disclosure the cylindrical light diffusers can be modeled to provide an irradiance pattern in a manner such that when the process is combined the individual exposures of each cylindrical light diffuser combine to produce a desired irradiance pattern "complete target" 8. It should be appreciated by those skilled in the art that the shape and size (cm$^2$) of irradiance pattern 8 are both important factors in achieving a complete target to treat a target tissue of a human being. In the example shown, the position of cylindrical light diffusers 1, 3 produce an irradiance pattern 8. Once the irradiance pattern is modeled, the number, size and arrangement of a subset of cylindrical light diffusers is chosen from the plurality of cylindrical light diffusers. The light flap is then removably positioned proximate the target tissue using the imaging data. The treatment plan can then be executed and completed without having to move or reposition the light emitting devices as will be disclosed in further detail herein below. It should be appreciated by those skilled in the art that the ability to complete the treatment plan with an apparatus that does not move relative to a patient has significant advantage over that of the prior art. Although only two cylindrical light diffusers are shown in this example, the modelling of any number of cylindrical light diffusers can be performed using the apparatus and methods of the present disclosure.

Figure 4:
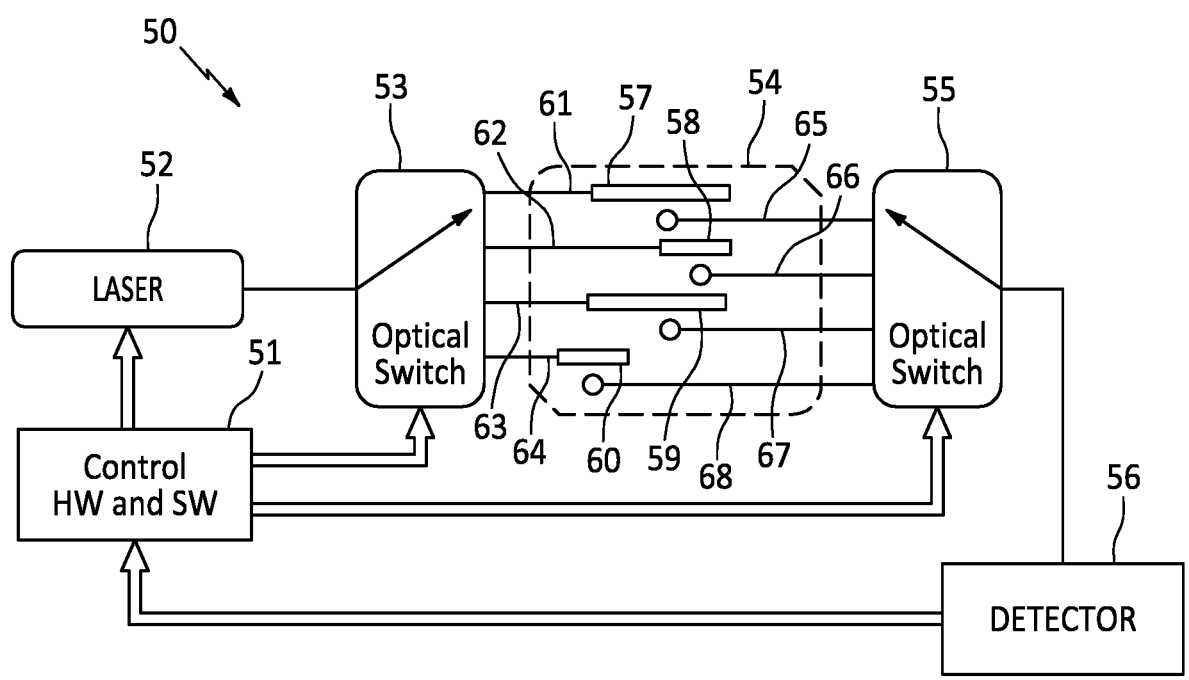
FIG. 4 is schematic representation of a PDT system in accordance with the present disclosure.

With reference to FIG. 4, there is shown an optical light delivery system in the form of a time multiplexed dosimetry (TMD) system 50 in accordance with certain embodiments of the current disclosure including a control system in the form of opto-electronic controller 51, light source 52, delivery optical switch 53, light flap 54, detector optical switch 55, and detector 56. In certain embodiments detector optical switch 55, and detector 56 can comprise a detection system. In certain embodiments, delivery optical switch 53 and detector optical switch 55 can comprise a micro-electromechanical system (MEMS) type optical switch allowing for higher reliability and ability to integrate with automation techniques. Light flap 54 can comprise any known type of light flap 54 and includes a plurality of cylindrical light diffusers fixedly positioned therein with only four such cylindrical light diffusers shown for clarity's sake. In the example shown, a subset of the plurality of cylindrical light diffusers, namely cylindrical light diffusers 57, 58, 59, 60 are optically coupled optical output channels of delivery optical switch 53 by delivery optical fibers 61, 62, 63, 64 respectively. In some embodiments, cylindrical light diffusers 57, 58, 59, 60 can comprise a 500-micron core. As shown in the figure, cylindrical light diffusers 57, 58, 59, 60 can have different lengths wherein the various lengths contribute to the configuring the irradiance pattern 8. It should be appreciated by those skilled in the art shorter cylindrical light diffusers 58, 60 will comprise a smaller individual irradiance pattern than longer cylindrical light diffusers 57, 59 and the lengths are selected to produce the desired overall irradiance pattern 8. One embodiment of a suitable delivery optical fiber is a 125-micron multi-mode graded index fiber. TMD system 50 further includes detector optical fibers 65, 66, 67, 68 optically connected to respective optical input channels of detector optical switch 55 and adapted to detect at least one optical parameter of actual therapy light emitted from cylindrical light diffusers 57, 58, 59, 60 respectively. In some embodiments, detector optical fibers 65, 66, 67, 68 can comprise a 500-micron core. One embodiment of a suitable detector optical fiber is an isotropic probe, for example Model IP-85 available from Rakuten Medical. Optical parameters can include the presence of light, power level, energy level, wavelength, diffusion pattern, etc. It should be noted that in this embodiment of TMD system 50, the position of cylindrical light diffusers 57, 58, 59, 60 and detector optical fibers 65, 66, 67, 68 are fixed relative to each other respectively and within flap 54. This aspect of the disclosure inventively enhances the calibration and accuracy of the detector optical fibers 65, 66, 67, 68 and the overall accuracy of TMD system 50 thereby. In the embodiment shown, each of the detector fibers has a paired respective cylindrical light diffuser wherein cylindrical light diffuser 57 is paired with detector optical fiber 65, cylindrical light diffuser 58 is paired with detector optical fiber 66, cylindrical light diffuser 59 is paired with detector optical fiber 67, and cylindrical light diffuser 60 is paired with detector optical fiber 68. In this particular embodiment, the single light source 52 is optically coupled to delivery optical switch 53 and detector optical switch 55 is optically coupled to a single detector 56. Controller 51 is configured to control delivery optical switch 53 and detector optical switch 55 in coordination such that the matched pairs of cylindrical light diffusers and detector optical fibers are in optical communication with light source 52 and optical detector 56 respectively. A suitable embodiment of light source 52 comprises a laser light source which can comprise a single semiconductor laser. Cylindrical light diffusers 57, 58, 59, 60 can be comprised of flexible cylindrical optical diffusers. Although this embodiment includes four cylindrical light diffusers 57, 58, 59, 60, other embodiments are contemplated having N diffusers wherein N can be four, more than four and fewer than four. It should be noted that cylindrical light diffusers 57, 58, 59, 60 are configured to cause light to spread evenly across a surface and are also known as light diffusers in many prior art illumination applications. Light flap 2 can comprise any suitable material having the flexibility to conform to a tissue surface and having the light transmissibility qualities to allow light emanating from cylindrical light diffusers 57, 58, 59, 60. Controller 51 includes a computer processor, a light device controller, software, and storage capability and is in electrical communication with light source 52, delivery optical switch 53, detector optical switch 55 and detector 56. Prior to use during a PDT procedure, the pairs of cylindrical light diffusers and detector optical fibers are calibrated to characterize the output power of the cylindrical light diffuser versus the detected power measured from the detector optical fiber.

As will be described in more detail herein after, TMD system 50 inventively uses a single light source 52 that is time multiplexed using delivery optical switch 53 to deliver therapy light dosage through multiple cylindrical light diffusers 57, 58, 59, 60 and further uses a single detector 56 that is also time multiplexed using detector optical switch 55 in coordination with the delivery optical switch to gather information related to the therapy light dosage delivered through the cylindrical light diffusers. One embodiment of detector 56 is Silicon (Si) free-space amplified photodetector such as model PDA 100A2 detector commercially available from Thorlabs. Controller 51 controls laser 52 and delivery optical switch 53 to control the amount of time, also referred to herein as the dwell time, each individual diffuser (cylindrical light diffuser 57, 58, 59, 60) receives therapy light as well as the power level of the laser to deliver a predetermined irradiance level (mW/cm$^2$), or brightness, to each diffuser during the dwell time. It should be appreciated by those skilled in the art that the irradiance level is selected to at least activate the particular type of photosensitizing drug being used. One embodiment of controller 51 is a multi-component processor board such a Raspberry Pi-4, 8 Gigabyte commercially available from CanaKit. During the dwell time for a particular diffuser, controller 51 further controls detector optical switch 55 to provide an optical connection to the respective detector fiber and is configured to provide a detector signal to detector 56. During operation of TMD 50, feedback output signals from detector 56 are provided to controller 51 and the controller sums the cumulative total power level delivered to each diffuser over the total dwell time to produce an average irradiance pattern over the entire target of interest in accordance with a predetermined photodynamic therapy plan. Controller 51 uses feedback output signals from detector 56 and employs an algorithm to produce the dwell times on each switch position in delivery optical switch 53 and power levels for the dwell time and passes the therapy light dosage on to the respective diffuser for each switch position. Controller 51 moves between switch positions in delivery optical switch 53 and detector optical switch 55 concurrently in a manner such that when the process is combined the individual exposures of each cylindrical light diffuser combine to produce the desired "complete target" of therapy light dosage delivery. Once the desired complete target of therapy light has been delivered that matches the predetermined treatment plan, controller 51 stops the process. Because TMD system 50 uses a plurality of cylindrical light diffusers, the position of the light emitting cylindrical light diffuser does not have to manipulated during the procedure as in the prior art. In addition, because TMD system 50 uses a single light source 52 and further uses a single detector 56, the system negates the requirement to calibrate multiple such sources and detectors. It should be noted by those skilled in the art that TMD system 50, when compared to systems of the prior art, significantly reduces the number of components which adds to overall reliability of the system.

Figure 5:
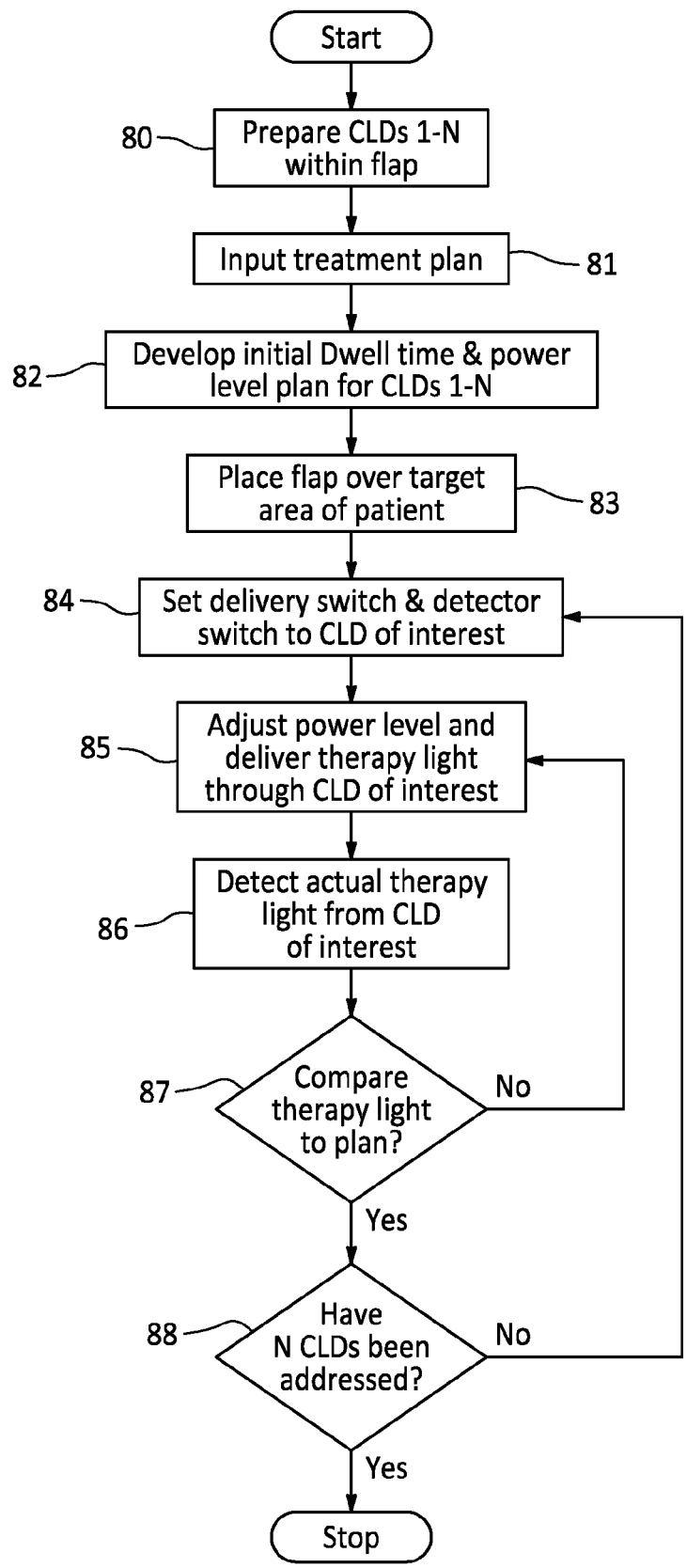
FIG. 5 is flow chart of a method for employing a light therapy system in accordance with the present disclosure.

With further reference to FIG. 5, in operation, TMD system 50 can advantageously operate in closed loop control. At step 80 cylindrical light diffusers 57, 58, 59, 60 are selected from a plurality of cylindrical light diffusers due to their position within longitudinal channels within flap 54 and therapy light emitting capability to provide the desired irradiance pattern as disclosed herein above. Although a subset of four cylindrical light diffusers are shown, any number of diffusers can be included up to N diffusers without departing from the scope of the present disclosure. In addition, the cylindrical light diffusers 57, 58, 59, 60 are fixedly positioned within flap 54, and unlike prior art methods, the predetermined locations within the flap remain static relative to a patient's body during the entire PDT procedure. At step 81, a user can provide controller 51 with a predetermined treatment plan that includes a desired target geometry and dosimetry plan. The target geometry can be comprised of magnetic resonance images, x-rays, etc. and can be in a digital form and referenced to a location on a patient's body. The dosimetry plan can be based on the treatment level desired, the type of photosensitizing drug and other relevant factors. At step 82, the computer processor of controller 51 can develop an initial dwell time plan and an initial power level plan for each of the cylindrical light diffusers 57, 58, 59, 60. Flap 54 can be placed over the target area of a patient at step 83, for example tissue or organ selected for PDT, and cylindrical light diffusers 57, 58, 59, 60 are controlled to provide an optimal irradiance pattern for the target area as disclosed herein above. At selecting step 84, and for each of the cylindrical light diffusers of interest, controller 51 can be configured to, starting with cylindrical light diffuser 57 for example, energize light source 52 to a predetermined power level to produce a therapy light, set delivery optical switch 53 to a channel that delivers the therapy light to delivery optical fiber 61 and to cylindrical light diffuser 57 where the therapy light is emitted from the cylindrical light diffuser at step 85 to a portion of the target area for an initial dwell time in accordance with detailed dwell time and power level control plan. At approximately the same time that delivery optical switch 53 is set to deliver the therapy light to delivery optical fiber 61, controller 51 sets detector optical switch 55 to a channel that and at detecting step 86 receives a portion of the actual therapy light from detector 65, including an actual power level indicator, which is converted by detector 56 to electrical feedback output signals that are transmitted to controller 51. At step 87, controller 51 tracks the dwell time of cylindrical light diffuser 57 and compares the predetermined power level to actual power level indicator and determines whether it meets the detailed dwell time and power level control plan. At step 87, if the delivered therapy light through the cylindrical light diffuser of interest does not meet the detailed dwell time and power level control plan, controller 51 can determine a new dwell time plan and an updated power level and can adjust the power level and dwell time for cylindrical light diffuser 57 based on the electrical signals transmitted by detector 56. If the power level matches the plan TMD system 50 continues to deliver therapy light to the cylindrical light diffuser of interest and continues to monitor the detected therapy light to ensure that the detailed dwell time and power level control plan are met for the cylindrical light diffuser of interest. At step 88, once the detailed dwell time and power level control plan are met for a particular cylindrical light diffuser of interest, controller 51 determines whether all of the plurality of cylindrical light diffusers 57, 58, 59, 60 have been addressed. Controller 51 of TMD system 50 can then move sequentially to select each of the remaining cylindrical light diffusers 58, 59, 60 and similarly control the therapy light delivered through each of the cylindrical light diffusers starting at back at step 84 in accordance with the detailed dwell time and power level control plan for the respective cylindrical light diffuser. The sequence of addressing each of the cylindrical light diffusers is not important so long as the individual detailed dwell time and power level control plan are met for the cylindrical light diffuser of interest and that all of the cylindrical light diffusers required to complete the predetermined treatment plan are similarly selectively addressed. Once all of the plurality of cylindrical light diffusers 57, 58, 59, 60 have been addressed, the therapy plan of TMD system 50 is stopped.

It is another aspect of this disclosure that TMD system 50 can be included in a PDT system that uses the desired irradiance patter, power levels and dwell times determined by controller 51 as attributes in a machine learning system. Such a PDT system is disclosed in co-pending patent cooperation treaty patent application serial number PCT/US21/23176 filed Mar. 19, 2021, the disclosure of which is included herein in its entirety. In such a system, controller 51 is further adapted to control a state of light output to the plurality of optical fibers 61, 62, 63, 64 wherein the state includes the power levels and dwell times in addition to other states disclosed.

As should be appreciated by those skilled in the art, TMD system 50 and methods for their use provide numerous benefits. The disclosed embodiments allow for the time multiplexing and power level control of a plurality of light emitting devices for PDT. Embodiments of the TMD disclosed provide accurate, stable, fast, finely and continuously adjustable delivery of therapy light to a target area.

All of the methods disclosed and claimed herein can be made and executed without undue experimentation in light of the present disclosure. While the apparatus and methods of this disclosure have been described in terms of preferred embodiments, it will be apparent to those of skill in the art that variations may be applied to the methods and in the steps or in the sequence of steps of the method described herein without departing from the concept, spirit and scope of the disclosure. In addition, modifications may be made to the disclosed apparatus and components may be eliminated or substituted for the components described herein where the same or similar results would be achieved. All such similar substitutes and modifications apparent to those skilled in the art are deemed to be within the spirit, scope, and concept of the invention.

Although the invention(s) is/are described herein with reference to specific embodiments, various modifications and changes can be made without departing from the scope of the present disclosure, as presently set forth in the claims below. Accordingly, the specification and figures are to be regarded in an illustrative rather than a restrictive sense, and all such modifications are intended to be included within the scope of the present disclosure. Any benefits, advantages, or solutions to problems that are described herein with regard to specific embodiments are not intended to be construed as a critical, required, or essential feature or element of any or all the claims.

Unless stated otherwise, terms such as "first" and "second" are used to arbitrarily distinguish between the elements such terms describe. Thus, these terms are not necessarily intended to indicate temporal or other prioritization of such elements. The terms "coupled" or "operably coupled" are defined as connected, although not necessarily directly, and not necessarily mechanically. The terms "a" and "an" are defined as one or more unless stated otherwise the terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system, device, or apparatus that "comprises," "has," "includes" or "contains" one or more elements possesses those one or more elements but is not limited to possessing only those one or more elements. Similarly, a method or process that "comprises," "has," "includes" or "contains" one or more operations possesses those one or more operations but is not limited to possessing only those one or more operations.

While the foregoing is directed to embodiments of the present disclosure, other and further embodiments of the disclosure may be devised without departing from the basic scope thereof, and the scope thereof is determined by the claims that follow.

What is claimed is:

1. A method for providing photodynamic therapy, the method comprising:
   determining an irradiance pattern for a target tissue;
   providing a flexible applicator flap having a plurality of parallel longitudinal channels disposed therein;
   providing a plurality of light emitting devices;
   positioning each of the plurality of light emitting devices at a predetermined location in a respective longitudinal channel of the plurality of parallel longitudinal channels;
   coupling a respective optical fiber to each of the plurality of light emitting devices;
   selecting a subset of light emitting devices from a plurality of light emitting devices to produce the irradiance pattern;
   determining a photodynamic therapy plan for each of the subset of light emitting devices;
   developing an initial dwell time plan and an initial power level plan for each of the subset of plurality of light emitting devices;
   positioning the flexible applicator flap at a predetermined position proximate the target tissue;
   selecting sequentially each of the subset of light emitting devices;
   delivering therapy light to the respective optical fibers of each of the subset of light emitting devices at an initial power level in accordance with the initial power level plan;
   detecting an optical parameter of an actual therapy light;
   comparing the optical parameter to the photodynamic therapy plan;
   adjusting the initial power level to an updated power level;
   calculating a new dwell time plan;
   summing a total dwell time and a total power level for each of the subset of light emitting devices; and
   completing the irradiance pattern in accordance with the photodynamic therapy plan.

2. The method for providing photodynamic therapy of claim 1, further comprising fixedly positioning the plurality of light emitting devices within the flexible applicator flap.

3. The method for providing photodynamic therapy of claim 1, wherein the selecting sequentially each of the subset of light emitting devices step comprises using an optical switch in optical communication with each of the plurality of optical fibers and in optical communication with a single laser light source.

4. The method for providing photodynamic therapy of claim 1, wherein the detecting an optical parameter of an actual therapy light step comprises using a plurality of detector fibers wherein each of the plurality of detector fibers is paired with a respective light emitting device of the subset of light emitting devices.

5. The method for providing photodynamic therapy of claim 4, further comprising selecting sequentially the plurality of detector fibers in coordination with the paired respective light emitting device.

6. The method for providing photodynamic therapy of claim 4, wherein the selecting a subset of light emitting devices from the plurality of light emitting devices step comprises modelling the irradiance pattern using imaging data of the target tissue and selecting the subset of light emitting devices from the plurality of light emitting devices to produce the irradiance pattern that substantially matches a geometry of the target tissue.

* * * * *